(12) United States Patent
Wu et al.

(10) Patent No.: US 8,195,408 B2
(45) Date of Patent: Jun. 5, 2012

(54) METHOD FOR SETTING UP SYSTEM OF REAGENT CHIP ANALYZER

(75) Inventors: Tzu-Chiang Wu, Sinshih Township, Tainan County (TW); Chien-Ho Chuang, Sinshih Township, Tainan County (TW); Tsung-Kai Chuang, Sinshih Township, Tainan County (TW); Jiann-Hua Wang, Sinshih Township, Tainan County (TW)

(73) Assignee: Kaiwood Technology Co., Ltd., Tainan County (TW)

( * ) Notice: Subject to any disclaimer, the term of this patent is extended or adjusted under 35 U.S.C. 154(b) by 1195 days.

(21) Appl. No.: 11/964,152

(22) Filed: Dec. 26, 2007

(65) Prior Publication Data
US 2009/0058617 A1 Mar. 5, 2009

(30) Foreign Application Priority Data
Sep. 4, 2007 (TW) ............................... 96132910 A

(51) Int. Cl.
*G01N 31/00* (2006.01)
(52) U.S. Cl. ..... 702/31; 702/30; 340/539.12; 422/82.05
(58) Field of Classification Search .................... 702/22, 702/27, 30, 31, 122, 123; 436/43, 46; 422/50, 422/530, 82.05
See application file for complete search history.

(56) References Cited

U.S. PATENT DOCUMENTS
7,667,603 B2 * 2/2010 Bolander et al. ........... 340/572.4
2005/0009122 A1 * 1/2005 Whelan et al. ............... 435/7.32
* cited by examiner

*Primary Examiner* — Manuel L Barbee
(74) *Attorney, Agent, or Firm* — Lin & Associates IP, Inc.

(57) ABSTRACT

A method for setting up a system of a reagent chip analyzer is provided. The method is adapted to modify parameters and testing conditions according to data of an authorization tag, so as to improve the adaptability range of the reagent chip analyzer for reagent chips of multiple specifications. The method includes: reading an identification code, authorization times, and specifications and analysis parameters of the reagent chip from an RFID tag; determining whether to load the specifications and the analysis parameters of the reagent chip according to the identification code and the authorization times; and if it is determined to load the specifications and the analysis parameters of the reagent chip, decreasing the authorization times by one, and analyzing the reagent chip according to the specifications and the analysis parameters of the reagent chip.

6 Claims, 2 Drawing Sheets

METHOD FOR SETTING UP SYSTEM OF REAGENT CHIP ANALYZER

BACKGROUND OF THE INVENTION

1. Field of the Invention

The present invention relates generally to a method for setting up a system, and in particular to a method for setting up a system of a reagent chip analyzer.

2. The Prior Arts

Biochemistry test is now a routine item of health check. Also, for the purpose of avoiding the damage caused by improper use of drugs or maintaining the fairness of sport competitions, test reagents are used by governmental departments or private enterprises for checking physical situations or detecting drug addictions.

A currently used test reagent is a reagent chip for checking urine, or blood, or serum. The reagent chip is a strip-shaped chip fabricated by biotechnology. The reagent chip is adapted for immunoassay whose result can be directly identified by naked eyes, according to the characteristic conjunction between antigens and antibodies. Unfortunately, assembly errors of the reagent chip often cause difficulties for alignment of lines. Therefore, the correctness of reading the result is often relied upon inspector's experience, and is often uncertain. Especially when a single color reaction line is weak and blur, test results obtained by different inspectors are often different.

As a solution, current inspections to the reagent chip are usually conducted by charge-coupled device (CCD) or complementary metal oxide semiconductor (CMOS) image sensors with corresponding software. The CCD or CMOS image sensor obtains an image of the color development on the reagent chip. The image is then inputted in a computer having a standardized color comparison program for comparing the color development on the reagent chip with the standardized color and obtaining the test result.

There are developed many types of reagent chips, such as a square flake chip. Usually, a conventional reagent chip analyzer is adapted for analyzing preselected reagent chips, e.g., of a certain specification. In such a reagent chip analyzer, the specification and analysis parameters of the reagent chips are preset or prestored in the reagent chip analyzer, and cannot be modified by the operator. Further, the conventional reagent chip analyzer often includes data of a certain reagent chip, and is adapted for testing the certain reagent chip and the test condition only.

SUMMARY OF THE INVENTION

An objective of the present invention is to provide a method for setting up a system of a reagent chip analyzer. The method is adapted to modify parameters and testing conditions according to data of an authorization tag, so as to improve the adaptability range of the reagent chip analyzer for reagent chips of multiple specifications.

Another objective of the present invention is to provide a method for setting up a system of a reagent chip analyzer. The method is adapted for eliminating unintended change to setting up statuses of the reagent chip analyzer by reading an identification code and authorization times stored in a radio frequency identification (RFID) tag, and counting the quantity of tested reagent chips by reading the authorization times.

For achieving the foregoing objectives, the present invention provides a method for setting up a reagent chip analyzer, adapted for testing a reagent chip according to an authorization tag, the authorization tag being an RFID tag. The method includes: reading an identification code, authorization times, and a specification and analysis parameters of the reagent chip from the RFID tag; determining whether to load the specification and the analysis parameters of the reagent chip according to the identification code and the authorization times; and if it is determined to load the specification and the analysis parameters of the reagent chip, decreasing the authorization times by one, and analyzing the reagent chip according to the specification and the analysis parameters of the reagent chip.

The method for setting up a reagent chip analyzer according to the present invention is adapted for adaptively testing multiple specifications of reagent chips by adjusting analysis parameters and testing conditions, so as to improve the adaptability of the reagent chip analyzer. The method according to the present invention is also adapted for eliminating unintended change to setting up statuses of the reagent chip analyzer, and for obtaining the number of the tested reagent chips by counting the authorization times.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
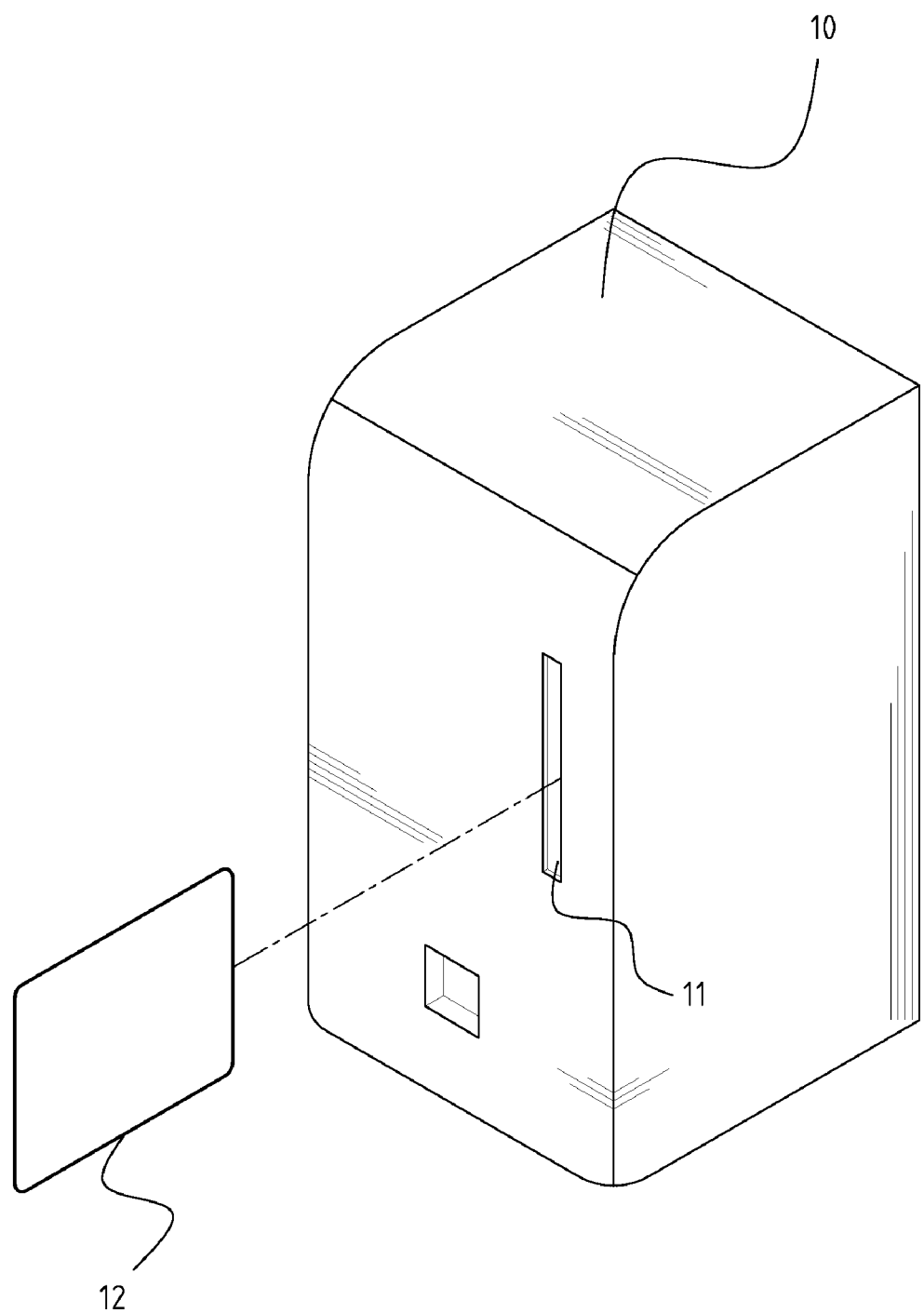
FIG. 1 is a schematic diagram illustrating an RFID tag being inserted in a reagent chip analyzer according to a preferred embodiment of the present invention.

FIG. 1 is a schematic diagram illustrating an RFID tag being inserted in a reagent chip analyzer according to a preferred embodiment of the present invention. Referring to FIG. 1, there is shown a casing 10 of a reagent chip analyzer. The casing 10 has a slot 11 configured corresponding to an RFID tag 12. There is also disposed an RFID tag reader (not shown) in the casing 10 corresponding to the slot 11. When the RFID tag 12 is inserted into the slot 11, the reagent chip analyzer obtains authorization setting data by using the RFID tag reader to read the RFID tag 12, so as to modify parameters and testing conditions of the regent chip analyzer.

Figure 2:
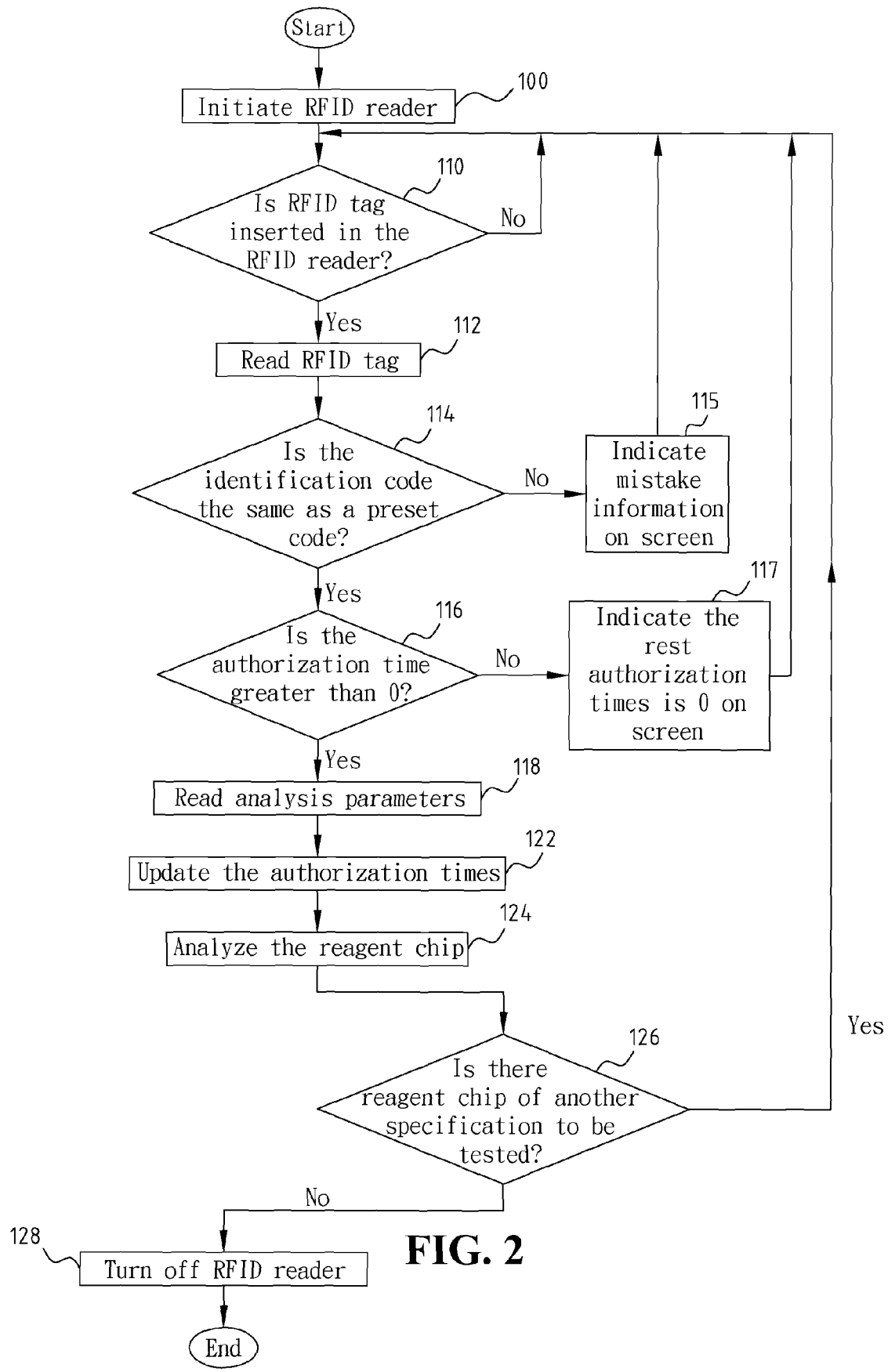
FIG. 2 is a flow chart illustrating a method for setting up a system of the reagent chip analyzer according to the present invention.

Then, referring to FIG. 2, there is shown a flow chart illustrating the method for setting up a system of the reagent chip analyzer according to the present invention. The method is adapted for a reagent chip analyzer for testing a reagent chip. In a preferred embodiment, at step 100, the RFID tag reader is initiated after the reagent chip analyzer is turned on and enters a standby status for preparation of test. At step 110, under the standby status, the RFID tag reader determines whether there is an RFID tag inserted therein; if it is determined that there is no RFID tag inserted, the standby status is sustained; if it is determined that there is an RFID tag inserted, the system conducts step 112. In an embodiment, the inserted RFID tag is required to be a legally authorized tag, which includes setting data of the reagent chip analyzer stored therein. The setting data includes an identification code, authorization times, and a specification and analysis parameters of the reagent chip. The analysis parameter may include but not limited to a quantity of regions to be tested, testing items, a size of the reagent chip, sizes of the regions to be tested, a calibration curve for the testing items, and a positive/negative determination threshold. At step 112, the reagent chip analyzer obtains the setting data recorded in the RFID tag by using the RFID tag reader to read the RFID tag, so as to read the identification code.

After reading the identification code, the system enters step 114, in which it is determined whether the identification code coincides with a preset code; if the identification code cannot be identified, or is determined as incompliant with the preset code, the system conducts step 115 to indicate mistake information on a screen. The mistake information reminds that the inserted RFID tag is not a legally authorized tag. When it is identified that the identification code is legally authorized or complies with the preset code, the system conducts step 116. The authorization times, which are the number of times that the reagent chip analyzer is allowed to test the reagent chip, are determined at step 116. Only when the number of the authorization times is greater than 0, i.e., the remaining number of times is greater than 0, the system enters a next step 118. Otherwise, the system enters step 117 to indicate information on the screen, e.g., indicating that the number of authorization times is 0 to remind the operator to obtain more authorization times for processing the reagent chip test.

At step 118, the specification and the analysis parameters of the reagent chip are loaded, or one kind of the reagent chip data recorded in the RFID tag is selected. The method for setting up a system of a reagent chip analyzer requires that only after identifying the identification code and confirming that the number of authorization times is greater than 0, the reagent chip analyzer enters step 118. After loading the specification and the analysis parameters, at step 122, the system updates and decreases the authorization times, e.g., minus 1 from the authorization times, feeds the decreased authorization times back to the RFID tag and records therein.

Thereafter, at step 124, the reagent chip is analyzed until the test ends. If there is another reagent chip of the same specification for test, the step 124 is repeated until the test ends.

After the test ends, if there is a further reagent chip of another specification to be tested, the system returns back to the step 110 to select another authorization tag or read another reagent chip data from the RFID tag. In such a way, the reagent chip analyzer is capable of modifying parameters and testing conditions for analyzing a reagent chip of another specification.

If at step 126, the operator terminates the operation of the system, then the system enters step 128 to turn off the RFID tag reader.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method for setting up a system of a reagent chip analyzer for analyzing multiple types of color development reagent chips according to an authorization tag that records multiple types of reagent chip data, the method comprising the steps of:
   (a) reading the reagent chip data of a selected type of reagent chips from the authorization tag by using the reagent chip analyzer, the reagent chip data comprising an identification code, authorization times and a specification and analysis parameters of the selected type of reagent chips;
   (b) determining whether to load the specification and the analysis parameters of the corresponding reagent chips according to the identification code and the authorization times;
   (c) if it is determined to load the specification and the analysis parameters of the corresponding reagent chips, decreasing the authorization times by one, and analyzing the corresponding reagent chips according to the specification and the analysis parameters of the corresponding reagent chips by using the reagent chip analyzer; and
   (d) if there is a different type of reagent chips to be tested, reading the reagent chip data of the different type of reagent chips from the authorization tag by using the reagent chip analyzer and returning to step (b).

2. The method according to claim 1, wherein the authorization tag is a radio frequency identification (RFID) tag.

3. The method according to claim 1, wherein the analysis parameters comprise a quantity of regions to be tested, testing items, a size of the reagent chip, sizes of the regions to be tested, a calibration curve for the testing items, and a positive/negative determination threshold.

4. The method according to claim 1, wherein step (c) further comprises: after decreasing the authorization times, feeding back and recording the decreased authorization times in the authorization tag.

5. The method according to claim 1, wherein in step (b) if it is determined to not load the specification and the analysis parameters, information indicating a mistake is displayed on a screen.

6. The method according to claim 1, wherein in step (b) it is determined to load the specification and the analysis parameters of the reagent chip when the identification code is correct and the number of the authorization times is greater than 0.

* * * * *